United States Patent [19]

Takahashi et al.

[11] Patent Number: 4,719,037

[45] Date of Patent: Jan. 12, 1988

[54] PIPERIDINE DERIVATIVES, PRODUCTION PROCESS THEREFOR, AND STABILIZERS FOR ORGANIC SUBSTANCES CONTAINING SAID DERIVATIVES AS AN ACTIVE COMPONENT

[75] Inventors: Yukoh Takahashi, Toyonaka; Yuzo Maegawa, Osaka; Hiroki Yamamoto, Nishinomiya; Tatsuo Kaneoya, Toyonaka; Haruki Okamura, Osaka; Shinichi Yachigo, Toyonaka; Tamaki Ishii, Suita, all of Japan

[73] Assignee: Sumitomo Chemical Company, Limited, Osaka, Japan

[21] Appl. No.: 887,813

[22] Filed: Jul. 21, 1986

[30] Foreign Application Priority Data

Aug. 7, 1985 [JP] Japan .................. 60-173817

[51] Int. Cl.$^4$ ................ C07D 401/14; C08K 5/34; C09D 7/06
[52] U.S. Cl. .................. 252/401; 252/402; 252/403; 524/103; 546/188
[58] Field of Search ............ 546/188; 252/401, 403, 252/402; 524/103

[56] References Cited

U.S. PATENT DOCUMENTS

| | | | |
|---|---|---|---|
| 4,415,688 | 11/1983 | Minagawa | 546/188 |
| 4,419,472 | 12/1983 | Berner et al. | 546/188 |
| 4,525,503 | 6/1985 | Cantatore | 546/188 |
| 4,532,279 | 7/1985 | Karrer | 546/188 |

FOREIGN PATENT DOCUMENTS 2849444  5/1980  Fed. Rep. of Germany ...... 546/188

*Primary Examiner*—Robert T. Bond
*Attorney, Agent, or Firm*—Stevens, Davis, Miller & Mosher

[57] ABSTRACT

Piperidine derivatives represented by the general formula (1)

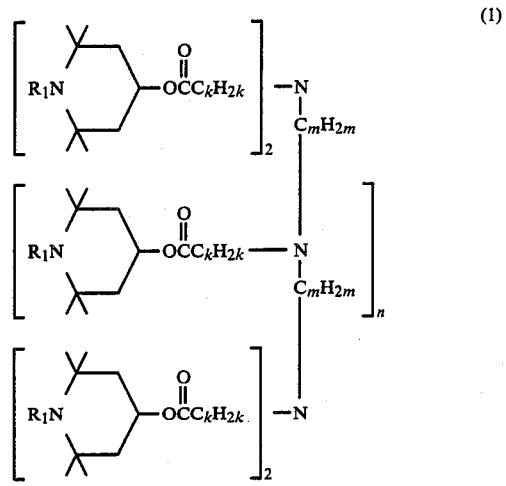

(wherein $R_1$ is a hydrogen atom, an alkyl group of 1 to 3 carbon atoms or an acyl group of 2 to 18 carbon atoms; and k, m and n each are independently an integer of 1 to 3), a process for producing said derivatives, and stabilizers for organic substances containing said derivatives as an active component.

36 Claims, No Drawings

PIPERIDINE DERIVATIVES, PRODUCTION PROCESS THEREFOR, AND STABILIZERS FOR ORGANIC SUBSTANCES CONTAINING SAID DERIVATIVES AS AN ACTIVE COMPONENT

BACKGROUND OF THE INVENTION

1. Field of the Invention

This invention relates to hindered amine type weathering agents (HALS) to be used in plastics, rubbers, paints, etc. More particularly, the present invention relates to novel piperidine derivatives, a process for producing said derivatives, and stabilizers for organic substances which contain said derivatives as an active component.

2. Description of the Prior Art

As well known, organic substances such as synthetic resins (e.g. polyethylenes, polypropylenes, polyvinyl chlorides, polyurethanes, ABS resins, etc.) and paints are deteriorated by lights causing softening, embrittlement and discoloration, etc. and resulting in significantly reduced physical properties.

In order to prevent such deterioration of organic substances by light, it has conventionally been known to use various light stabilizers in organic substances, such as 2-hydroxy-4-methoxybenzophenone, 2-hydroxy-4-octoxybenzophenone, 2-(2-hydroxy-5-methylphenyl)-benzotriazole, 2-(2-hydroxy-3-t-butyl-5-methylphenyl) 5- chlorobenzotriazole, 2-(2-hydroxy-3,5-dipentylphenyl) benzotriazole, ethyl 2-cyano-3,3-diphenylacrylate, 2,4-di-t-butylphenyl 3,5-di-t-butyl-4hydroxybenzoate, [2,2'-thiobis(4-t-octylphenolato)]-n-butylamine. Ni (II), nickel salt of bis(3,5-di-t-butyl-4-hydroxybenzylphosphoric acid monoethyl ester), bis(2,2,6,6-tetramethyl-4-piperidyl) sebacate and the like. However, these light stabilizers are not sufficienly satisfactory.

SUMMARY OF THE INVENTION

In view of the above situation, the present inventors made an extensive study in order to find a solution for the above problem. As a result, it has been found that the piperidine derivatives represented by the following general formula (1) are very effective in preventing the light deterioration of organic substances such as synthetic resins, paints and the like. The finding has led to the completion of the present invention.

The present invention relates to piperidine derivatives represented by the general formula (1)

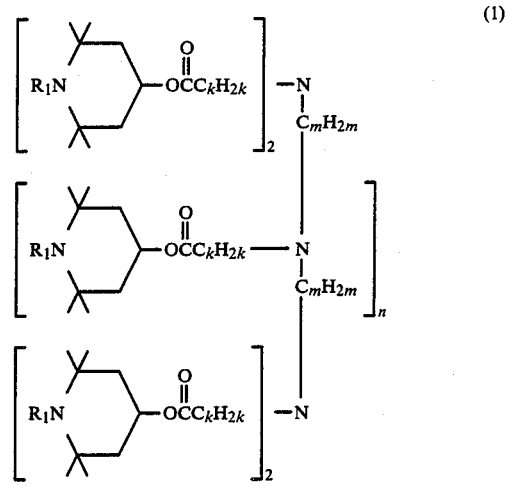

(wherein $R_1$ is a hydrogen atom, an alkyl group of 1 to 3 carbon atoms or an acyl group of 2 to 18 carbon atoms; and k, m and n each are independently an integer of 1 to 3), a process for producing said derivatives, and stabilizers for organic substances which contain said derivatives as an active component.

DETAILED DESCRIPTION OF THE INVENTION

The present piperidine derivatives represented by the general formula (1) are novel compounds synthesized for the first time by the present inventors and can easily be produced, for example, by reacting a carboxylic acid derivative represented by the general formula (2)

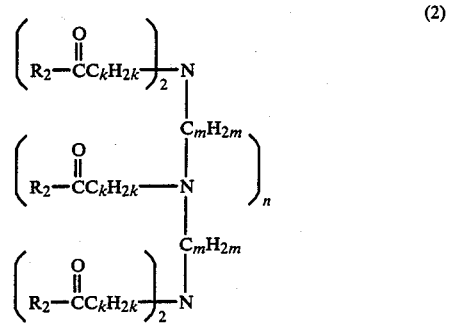

(wherein $R_2$ is a hydroxyl group, an alkoxyl group of 1 to 4 carbon atoms or a halogen atom selected from the group consisting of Cl, Br, I, etc.; and k, m and n each are independently an integer of 1 to 3) and a piperidinol derivative represented by the general formula (3)

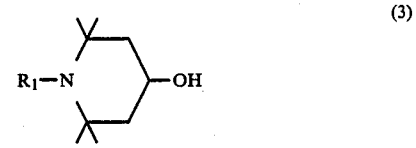

(wherein $R_1$ is an alkyl group of 1 to 3 carbon atoms or an acyl group of 2 to 18 carbon atoms).

Specific examples of $R_1$ includ alkyl grups such as methyl group, ethyl group, propyl group and the like, as well as acyl groups such as acetyl group, propinonyl group, butanoyl group, hexanoyl group, decanoyl group, dodecanoyl group, octadecanoyl group and the like. Specific examples of $R_2$ include alkoxyl groups such as methoxy group, ethoxy group, butoxy group and the like, as well as halogen atoms such as Cl, Br, I and the like.

When $R_2$ of the general formula (2) is a hydroxyl group, the above reaction can be conducted in a solvent or in a solvent-free state. Specific examples of the solvent include cyclic and non-cyclic aliphatic hydrocarbons such as n-hexane, isooctane, cyclopentane, cyclohexane and the like, as well as aromatic hydrocarbons such as benzene, toluene, xylene, propylbenzene and the like. These solvents can be used singly or in combination. Preferable of these are n-heptane and toluene.

The reaction is ordinarily conducted in the presence of an acidic catalyst. Specific examples of the acidic catalyst include mineral acids such as hydrochloric acid, sulfuric acid, nitric acid, phosphoric acid and the like; aromatic sulfonic acids such as benzenesulfonic acid, toluenesulfonic acid, naphthalenesulfonic acid and the like; and aliphatic sulfonic acids such as methanesulfonic acid, ethanesulfonic acid and the like. Preferable of these is toluensulfonic acid.

The catalyst is used in an amount of 0.01 to 10 moles, preferably 0.3 to 3 moles per 1 mole of the piperidinol derivative represented by the general formula (3).

The reaction is conducted at a temperature of 0° to 200° C, preferably 60° to 160° C. Ordinarily it is conducted at the boiling point of the solvent used.

The mole ratio of the carboxylic acid derivative represented by the general formula (2) and the piperidinol derivative represented by the general formula (3) both used in the reaction is 1: 4.5 to 1:10 when n is 1, 1:5.5 to 1:12 when n is 2 and 1:6.5 to 1:14 when n is 3.

The solvent is used in a desired amount. However, it is ordinarily used in an amount of 0 to 20 times, preferably 0 to 8 times the weight of the carboxylic acid derivative represented by the general formula (2).

After the completion of the reaction, the catalyst used is removed by a method such as filtration, water washing or the like, and then the solvent used is distilled off to obtain a product.

When $R_2$ of the general formula (2) is an alkoxyl group, the reaction can be conducted in a solvent or in a solvent-free state. As the solvent, there can be used cyclic and non-cyclic aliphatic hydrocarbons such as n-hexane, isooctane, cyclopentane, cyclohexane and the like; cyclic and non-cyclic aliphtic ethers such as propyl ether, amyl ether, tetrahydrofuran, dioxane, methyl cellosolve and the like; aromatic hydrocarbons such as benzene, toluene, xylene, propylbenzene and the like; alcohols such as methanol, ethanol, propanol, isopropanol, butanol, isobutanol and the like; water-soluble polar solvents such as N,N-dimethylformamide, dimethyl sulfoxide, sulfolane and the like; and halogenated hydrocarbons such as dichloromethane, chloroform and the like. Preferable of these are n-heptane, n-octane and toluene.

The reaction is an ester exchange reaction and can ordinarily be promoted by the use of a basic catalyst. As the basic catalyst, there can be mentioned, for example, metal hydroxides such as sodium hydroxide, potassium hydroxide, lithium hydroxide and the like; metal hydrides such as sodium boron hydride, sodium hydride, lithium hydride and the like; metal amides such as sodium amide, potassium amide, lithium amide, and the like; and alkali metal alkoxides and alkali metal phenoxides such as potassium t-butoxide, sodium methoxide, sodium phenoxide and the like. Preferable of these catalysts are potassium butoxide, lithium amide, sodium hydroxide, etc.

The catalyst is used in an amount of 0.001 to 10 moles, preferably 0.003 to 3 moles per 1 mole of the piperidinol derivative represented by the general formula (3).

The reaction is conducted at a temperature of 0° to 200° C., preferably 60° to 160° C.

The mole ratio of the carboxylic acid derivative represented by the general formula (2) and the piperidinol derivative rpresented by the general formula (3) is 1:4.5 to 1:10 when n is 1, 1:5.5 to 1:12 when n is 2 and 1:6.5 to 1:14 when n is 3.

The solvent can be used in a desired amount. However, it is ordinarily used in an amount of 0 to 20 times, preferably 0 to 8 times the weight of the carboxylic acid derivative represented by the general formula (2).

After the completion of the reaction, the catalyst used is removed by a method such as filtration, water washing or the like, and then the solvent used is distilled off to obtain a product.

When $R_2$ of the general formula (2) a halogen atom, the reaction is conducted in an inert solvent in the presence of a dehydrohalogenating agent.

Specific examples of the inert solvent include cyclic and non-cyclic aliphatic hydrocarbons such as n-hexane, n-heptane, isooctane, nonane, cyclopentane, cyclohexane and the like; cyclic and non-cyclic alipatic ethers such as propyl ether, amyl ether, tetrahydrofuran, dioxane, methyl cellosolve and the like; aromatic hydrocarbons such as benzene, toluene, xylene, propylbenzene and the like; halogenated hydrocarbons such as dichloromethane, chloroform and the like; and esters such as ethyl acetate, butyl acetate and the like. These solvents can be used singly or in combination. Preferable of these are toluene, ethyl acetate and tetrahydrofuran.

As the dehydrohalogenating agent, there can be mentioned, for example, tertiary amines (e.g. triethylamine, dimethylaniline, N,N-dimethylbenzylamine, tetramethylurea), pyridine derivatives [e.g. pyridne, 4-(N,N-dimethylamino)pyridine]and metal carbonates (e.g. sodium carbonate, potassium hydrogen carbonate). Preferable of these are triethylamine and pyridine.

It is possible that no such dehydrohalogenating agent be used and the piperidinol derivative represented by the general formula (3) be used as a dehydrohalogenating agent.

The dehydrohalogenating agent is used in an amount of 0.8 to 1.2 moles, preferably 0.9 to 1.1 moles per 1 mole of the piperidinol derivative represented by the general formula (3).

The mole ratio of the carboxylic acid derivative represented by the general formula (2) and the piperidinol derivative represented by the general formula (3) is 1:4.5 to 1:6.0 when n is 1, 1:5.4 to 1:7.2 when n is 2 and 1:6.3 to 1:8.4 when n is 3.

The reaction is conducted at a temperature of −30° to 120° C., preferably −10° to 80° C.

The solvent is used in a desired amount. However, it is ordinarily used in an amount of 0.1 to 30 times, preferably 0.3 to 10 times the weight of the carboxylic acid derivative represented by the general formula (2).

After the completion of the reaction, substances such as a salt formed by a reaction between hydrogen halide and the dehydrohalogenating agent are removed by a method such as filtration, water washing or the like, and then the solvent is distilled off to obtain a product.

The product thus obtained can be purified by a known method such as recrystallization, solvent washing, chromatography or the like.

Specific examples of the present piperidine derivative thus obtained are shown below.

Pentakis(2,2,6,6-tatramethyl-4-piperidyl) diethylenetriamine-N,N,N',N'',N''-pentaacetate
Pentakis(1,2,2,6,6-pentamethyl-4-piperidyl) diethylenetriamine-N,N,N',N'',N''-pentaacetate
Pentakis(1-propyl-2,2,6,6-tetramethyl-4-piperidyl) diethylenetriamine-N,N,N',N'',N''-pentaacetate
Pentakis(1-acetyl-2,2,6,6-tetramethyl-4-piperidyl) diethylenetriamine-N,N,N',N'',N''-pentaacetate
Pentakis(1-butanoyl-2,2,6,6-tetramethyl-4-piperidyl) diethylenetriamine-N,N,N',N'',N''-pentaacetate
Pentakis(1-octanoyl-2,2,6,6-tetramethyl-4-piperidyl) diethylenetriamine-N,N,N',N'',N''-pentaacetate
Pentakis(1-dodecanoyl-2,2,6,6-tetramethyl-4-piperidyl) diethylenetriamine-N,N,N',N'',N''-pentaacetate
Pentakis(1-octadecanoyl-2,2,6,6-tetramethyl-4-piperidyl) diethylenetriamine-N,N,N',N'',N''-pentaacetate
Pentakis(2,2,6,6-tetramethyl-4-piperidyl) dipropylenetriamine-N,N,N',N'',N''-pentaacetate
Pentakis(1,2,2,6,6-pentamethyl-4-piperidyl) dipropylenetriamine-N,N,N',N'',N''-pentaacetate
Pentakis(1-acetyl-2,2,6,6-tetramethyl-4-piperidyl) dipropylenetriamine-N,N,N',N'',N''-pentaacetate
Pentakis(1-octadecanoyl-2,2,6,6-tetramethyl-4-piperidyl) dipropylenetriamine-N,N,N',N'',N''-pentaacetate
Pentakis(2,2,6,6-tetramethyl-4-piperidyl) diethylenetriamine-N,N,N',N'',N''-pentapropionate
Pentakis(1,2,2,6,6-pentamethyl-4-piperidyl) diethylenetriamine-N,N,N',N'',N''-pentapropionate
Pentakis(1-octadecanoyl-2,2,6,6-tetramethyl-4-piperidyl) diethylenetriamine-N,N,N',N'',N''-pentapropionate
Hexakis(2,2,6,6-tetramethyl-4-piperidyl) triethylenetetramine-N,N,N',N'',N''',N''''-hexaacetate
Hexakis(1,2,2,6,6-pentamethyl-4-piperidyl) triethylenetetramine-N,N,N',N'',N''',N''''-hexaacetate
Hexakis (1-propyl-2,2,6,6-pentamethyl-4-piperidyl) triethylenetetramine-N,N,N',N'',N''',N''''-hexaacetate
Hexakis(1-acetyl-2,2,6,6-pentamethyl-4-piperidyl) triethylenetetramine-N,N,N', N'', N''', N''40 -hexaacetate
Hexakis (1octanoyl-2,2,6,6-pentamethyl-4-piperidyl) triethylenetetramine-N,N,N,', N'',N''',N''''-hexaacetate
Hexakis(1-dodecanoyl-2,2,6,6-pentamethyl-4-piperidyl) triethylenetetramine-N,N,N',N'',N''',N''''-hexaacetate
Hexakis(1-octadecanoyl-2,2,6,6-pentamethyl-4-piperidyl) triethylenetetramine-N,N,N',N'',N''',N''''-hexaacetate
Hexakis(2,2,6,6-tetramethyl-4-piperidyl) tripropylenetetramine-N,N,N',N'',N''',N''''-hexapropionate
Hexakis(1,2,2,6,6-pentamethyl-4-piperidyl) tripropylenetetramine-N,N,N',N'',N''',N''''-hexapropionate
Hexakis(1-octadecanoyl-2,2,6,6-tetramethyl-4-piperidyl) tripropylenetetramine-N,N,N',N'',N''',N''''-hexapropionate
Heptakis(2,2,6,6-tetramethyl-4-piperidyl) tetraethylenepentamine-N,N,N',N'',N''',N''''-heptapropionate
Heptakis(2,2,6,6-tetramethyl-4-piperidyl) tetrapropylenepentamine-N,N,N',N'',N''',N''''-heptaacetate
Heptakis(2,2,6,6-tetramethyl-4-piperidyl) tetraethylenepentamine-N,N,N',N'',N''',N''''-heptapropionate
Heptakis(2,2,6,6-tetramethyl-4-piperidyl) tetrapropylenepentamine-N,N,N',N'',N''',N''''-heptapropionate Of these piperidines, preferable as a stabilizer for synthetic resins and paints are pentakis(2,2,6,6-tetramethyl-4-piperidyl) diethylenetriamine-N,N,N',N'',N''-pentaacetate, pentakis(1,2,2,6,6-pentamethyl-4-piperidyl) diethylenetriamine-N,N,N',N'',N''-pentaacetate, hexakis(2,2,6,6-tetramethyl-4-piperidyl) triethylenetetramine-N,N,N',N'',N''',N''''-hexaacetate and hexakis(1,2,2,6,6-pentamethyl-4-piperidyl) triethylenetetramine-N,N,N',N'',N''40,N'''-hexaacetate. And particularly preferable are pentakis (2,2,6,6-tetramethyl-4-piperidyl) diethylenetriamine-N,N,N',N'',N''-pentaacetate and pentakis(1,2,2,6,6-pentamethyl-4-piperidyl) diethylenetriamine-N,N,N',N'',N''-pentaacetate.

In using the present piperidine derivatives as a stabilizer for organic substances such as synthetic resins or paints, said derivatives are incorporated into synthetic resins or paints in an amount of ordinarily 0.01 to 5 parts by weight, preferably 0.05 to 2 parts by weight per 100 parts by weight of synthetic resin or paint. The incorporation is conducted using substantially the same apparatus and procedure as those known in incorporating a stabilizer, a pigment, a filler, etc. into a synthetic resin or a paint.

The present stabilizers may be used in combination with other additives such as a light stabilizer, a metal deactivator, a metal soap, a nucleating agent, a lubricant, an antistatic agent, a flame retarder, a pigment, a filler and the like.

Combination use with a phenolic antioxidant, in particular, can improve the thermal and oxidation stability of synthetic resins or paints. As the phenolic antioxidant, there can be mentioned, for example, 2,6-di-t-butyl-4-methylphenol, n-octadecyl 3-(3,5-di-t-butyl-4-hydroxyphenyl) propionate, 1,1,3-tris(2-methyl-4-hydroxy-5-t-butylphenyl)butane, 1,3,5-trimethyl-2,4,6-tris (3,5-di-t-butyl-4-hydroxybenzyl)benzene, 1,3,5-tris(3,5-di-t-butyl-4-hydroxybenzyl) isocyanurate, 1,3,5-tris[3-(3,5-di-t-butyl-4-hydroxyphenyl) propionyloxyethyl]isocyanurate, 1,3,5-tris(2,6-dimethyl-3-hydroxy-4-t-butylbenzyl) isocyanurate, pentaerythritol tetrakis[3-(3,5-di-t-butyl-4-hydroxyphenyl)propionate], tetrakis[3-(3-t-butyl-5-methyl-4-hydroxyphenyl)propionate]and 2,2'-methylenebis(6-t-butyl-4-methylphenol) monoacrylate.

Combination use with a phosphite type antioxidant can improve the color of synthetic resins and paints. As the phosphite type antioxidant, there can be mentioned, for example, tris(nonylphenyl) phosphite, distearylpentaerythritol diphosphite, tris(2,4-di-t-butylphenyl) phosphite, tris(2-t-butyl-4-methylphenyl) phosphite, bis(2,4-di-t-butylphenyl)pentaerythritol diphosphite and tetrakis(2,4-di-t-butylphenyl)-4,4'-biphenylene diphosphite.

Combination use is also possible with a sulfur type antioxidant such as dilaurylthiodipropionate, dimyristylthiodipropionate, distearylthiodipropionate or pentaerythritol tetrakis(3-laurylthiopropionate).

The synthetic resins which can be stabilized by the present stabilizers include, for example, low density polyethylenes, high density polyethylenes, linear low density polyethylenes, chlorinated polyethylenes, polypropylenes, polyvinyl chlorides, EVA resins, PMMA resins, polystyrenes, high impact polystyrenes, ABS resins, AES resins, MBS resins, polyethylene terephthalates, polybutyelene terephthalates, polyamides, polyimides, polycarbamates, polyacetals, polyurethanes, unsaturated polyester resins, and blends between one of said resins and a rubber (e.g. an isoprene rubber, a butadiene rubber, an acrylonitrile-butadiene copolymer rubber, a styrenebutadiene copolymer rubber, an ethylene-propylene copolymer rubber). The paints which can be stabilized by the present stabilizers include oil paints, alcohol paints, cellulose derivative paints, synthetic resin paints, synthetic resin emulsion paints, aqueous baking paints, etc.

The present invention will specifically be described below by way of Examples. However, the invention is in no way restricted to these Examples.

EXAMPLE 1

Production of compound I-1

In a 1-liter flask equipped with a thermometer, a stirrer and a Dean-Stark trap were placed 46.35 g (0.1 mole) of pentamethyldiethylenetriamine pentaacetate, 86.49 g (0.55 mole) of 2,2,6,6-tetramethyl-4-piperidinol, 200 g of n-heptane and 0.11 g (0.005 mole) of lithium amide. The temperature inside the flask was increased and methanol formed with the progress of reaction was removed by the Dean-Stark trap. Reaction was conducted for further 4 hours under refluxing.

After the completion of the reaction, the contents of the flask were cooled to 60° C. Thereto was added 50 g of hot water of 60° C. to wash the n-heptane layer. Then, the water layer was separated. The n-heptane layer was subjected to vacuum distillation to remove the n-heptane. The residue was recrystallized to obtain 87.17 g (yield: 80%) of a white crystal of pentakis(2,2,6,6-tetramethyl-4-piperidyl) diethylenetriamine-N,N,N',N'',N''-pentaacetate.

Melting point: 87° to 89° C.

Elementary analysis of $C_{59}H_{108}N_8O_{10}$: The figures in parentheses are calculated values. C: 65.10% (65.04%), H: 10.04% (9.99%), N: 10.29% (10.28%).

Field desorption mass spectrometry: A parent peak was confirmed at 1088.

EXAMPLE 2

Production of compound I-2

In a 1-liter flask equipped with a thermometer, a stirrer and a cooling tube were placed 89.49 g (0.55 mole) of 2,2,6,6-tetramethyl-4-piperidinol, 55.65 g (0.55 mole) of triethylamine and 400 ml of toluene. Stirring was started at room temperature. Thereto was dropwise added in 2 hours a solution of 48.56 g (0.1 mole) of triethylenetetramine hexaacetyl chloride dissolved in 100 ml of toluene. During this time, the flask was kept in a water bath so that the reaction heat generated could be absorbed and the temperature inside the flask could be kept at 60° C. or below.

After the completion of the dropping, the reaction mixture was washed with hot water of 60° C. and the water layer was separated. The toluene layer was subjected to vacuum distillation to remove the toluene. The remaining yellow oily matter was purified by silica gel column chromatography to obtain 81.83 g (Yield: 62%) of hexakis(2,2,6,6-tetramethyl-4-piperidyl) triethylenetetramine-N, N,N',N'',N''',N''''-hexaacetate as a yellow glassy product.

Elementary analysis of $C_{72}H_{132}N_{10}O_{12}$: The figures in parentheses are calculated values. C: 65.09% (65.03%), H: 9.98% (10.00%), N: 10.49% (10.53%).

Field desorption mass spectrometry: A parent peak was confirmed at 1328.

EXAMPLE 3

Production of compound I-3

In a 1-liter flask similar to the one used in Example 2 were placed 89.92 g (0.525 mole) of 1,2,2,6,6-pentamethyl-4-piperidinol, 41.53 g (0.525 mole) of pyridine and 400 ml of ethyl acetate. Stirring was started at room temperature. Thereto was dropwise added in 3 hours a solution of 61.11 g (0.1 mole) of triethylenetetramine hexaacetyl chloride dissolved in 100 ml of ethyl acetate. During this time, the flask was kept in a water bath so that the reaction heat generated could be absorbed and the temperature inside the flask could be kept at 60° C. or below.

After the completion of the dropping, the reaction mixture was washed with hot water of 60° C. and the water layer was separated. The ethyl acetate layer was subjected to vacuum distilation to remove the ethylacetate. The remaining yellow oily substance was purified by silica gel column chromatography to obtain 99.68 g (yield: 71%) of hexakis(1,2,2,6,6-pentamethyl-4-piperidyl) triethylenetramine-N,N,N',N'',N''',N''''-hexaacetate as a light yellow oily product.

Elementary analysis of $C_{78}H_{134}N_{10}O_{12}$: The figures in parentheses are calculated values. C: 66.29% (66.25%), H: 10.31% (10.26%), N: 9.99% (9.91%).

Field desorption mass spectrometry: A parent peak was confirmed at 1412.

EXAMPLE 4

The following compounding materials were mixed according to the following formulation for 5 minutes by a mixer and then melt-kneaded by a mixing roll of 180° C. to obtain various resin compounds. Each resin compound was molded into a sheet of 1 mm in thickness by a hot press of 210° C. Test pieces each of 150 mm×30 mm×1 mm were prepared from these sheets.

The test pieces were subjected to light exposure in a sunshine weatherometer (light source: carbon arc, black panel temperature: 83±3° C., spray interval: 120 minutes, spray time: 18 minutes). They were bent every 60 hours, and a time when each test piece was cut by bending was measured as the weathering performance of each resin compound.

The results are shown in Table 1.

| Compounding formulation | |
|---|---|
| Unstabilized polypropylene | 100 parts by weight |
| Calcium stearate | 0.1 parts by weight |
| 2,6-di-t-butyl-4-methylphenol | 0.05 parts by weight |
| Test compound (light stabilizer) | 0.15 parts by weight |

In Table 1, LS-1 and LS-2 refer to the following compounds.

LS-1: 2-(2-Hydroxy-3-t-butyl-5-methylphenyl) 5-chlorobenzotriazole

LS-2: Bis(2,2,6,6-tetramethyl-4-piperidyl) sebacate

TABLE 1

| Resin compound No. | Test compound (light stabilizer) | Weathering performance (hours) |
|---|---|---|
| 1 | I-1 (this invention) | 1,320 |
| 2 | I-2 (this invention) | 1,200 |
| 3 | I-3 (this invention) | 1,260 |
| 4 | LS-1 (comparison) | 360 |
| 5 | LS-2 (comparison) | 960 |
| 6 | No addition | 120 |

EXAMPLE 5

Resin compound each having the follwoing formulation were extruded at 200° C. to prepare pellets. The pellets were subjected to injection molding at 230° C. to prepare test pieces each of 2 mm in thickness.

The test pieces were subjected to light exposure for 1,500 hours in a fadeometer (light source: ultraviolet carbon arc, black panel temperature: 63±3° C.), and the color change of each test piece was evaluated as a color difference ΔYI before and after the light exposure.

The results are shown in Table 2.

| Resin compound formulation | |
|---|---|
| ABS resin | 100 parts by weight |
| Pentaerythritol tetrakis[3-(3,5-di-t-butyl-4-hydroxyphenyl)propionate] | 0.05 parts by weight |
| Distearyl 3,3'-thiodipropionate | 0.2 parts by weight |
| Test compound (light stabilizer) | 0.2 parts by weight |

TABLE 2

| Resin compound No. | Test compound (light stabilizer) | ΔYI |
|---|---|---|
| 1 | I-1 (this invention) | 12.2 |
| 2 | I-2 (this invention) | 12.9 |
| 3 | I-3 (this invention) | 13.1 |
| 4 | LS-1 (comparison) | 29.5 |
| 5 | LS-2 (comparison) | 28.6 |
| 6 | No addition | 44.2 |

What is claimed is:

1. A piperidine represented by the formula (1)

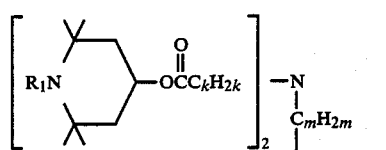
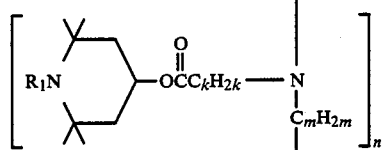
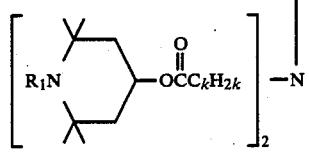
(1)

(wherein $R_1$ is a hydrogen atom, an alkyl group of 1 to 3 carbon atoms or a $C_1$–$C_{17}$ alkylcarbonyl group and k, m and n each are an integer of 1 to 3).

2. A piperidine according to claim 1, which is pentakis (2,2,6,6-tetramethyl-4-piperidyl) diethylenetriamine-N,N,N',N'',N''-pentaacetate.

3. A piperidine according to claim 1, which is pentakis (1,2,2,6,6-pentametyl-4-piperidyl) diethylenetriamine-N,N,N',N'', N''-pentaacetate.

4. A piperidine according to claim 1, which is hexakis (2,2,6,6-tetramethyl-4-piperidyl) triethylenetetramine-N,N,N',N'',N''',N'''-hexaacetate.

5. A piperidine according to claim 1, which is hexakis (1,2,2,6,6-pentamethyl-4-piperidyl) triethylenetetramine-N,N,N',N'',N''',N'''-hexaacetate.

6. A process for producing a piperidine composition represented by the formula (1)

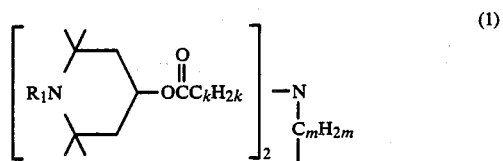
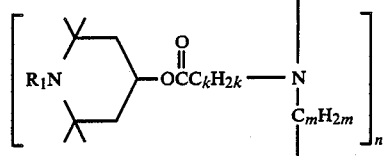
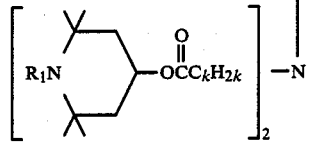
(1)

(wherein $R_1$ is an alkyl group of 1 to 3 carbon atoms or $C_1$–$C_{17}$ alkylcarbonyl group and k, m and n each are independently an integer of 1 to 3), the process comprising reacting a carboxylic acid represented by formula (2)

(2)

(wherein $R_2$ is a hydroxyl group, an alkoxyl group of 1 to 4 carbon atoms or a halogen atom selected from the group consisting of Cl, Br and I; and k, m and n each have the same definition as given previously) with a piperidinol represented by formula (3)

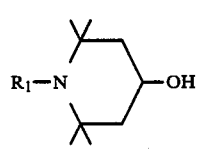
(3)

(wherein $R_1$ has the same definition as given previously), in a solvent or in a solvent-free state in the presence of a catalyst.

7. A process according to claim 6, wherein $R_2$ of the carboxylic acid represented by formula (2) is a hydroxyl group and the reaction is conducted in the presence of an acidic catalyst.

8. A process according to claim 7, wherein the acidic catalyst is a mineral acid, an aromatic sulfonic acid or an aliphatic sulfonic acid.

9. A process according to claim 7, wherein the acidic catalyst is used in an amount of 0.01 to 10 moles per 1 mole of the piperidinol represented by formula (3).

10. A process according to claim 7, wherein the reaction is conducted at a temperature of 0° to 200° C.

11. A process according to claim 7, wherein the solvent is used in an amount of 0 to 20 times the weight of the carboxylic acid represented by formula (2).

12. A process according to claim 7, wherein the mole ratio of the carboxylic acid represented by formula (2) and the piperidinol represented by formula (3) is 1:4.5 to 1:10 when n is 1, 1:5.5 to 1:12 when n is 2 and 1:6.5 to 1:14 when n is 3.

13. A process according to claim 6, wherein $R_2$ of the carboxylic acid represented by formula (2) is an alkoxyl group and the reaction is conducted in the presence of a basic catalyst.

14. A process according to claim 13, wherein the basic catalyst is a metal hydroxide, a metal hydride, a metal amide, an alkali metal alkoxide or an alkali metal phenoxide.

15. A process according to claim 13, wherein the basic catalyst is used in an amount of 0.001 to 10 moles per 1 mole of the piperidinol represented by the formula (3).

16. A process according to claim 13, wherein the reaction is conducted at a temperature of 0° to 200° C.

17. A process according to claim 13, wherein the solvent is used in an amount of 0 to 20 times the weight of the carboxylic acid represented by general formula (2).

18. A process according to claim 13, wherein the mole ratio of the carboxylic acid represented by the formula (2) and the piperidinol represented by the general formula (3) is 1:4.5 to 1:10 when n is 1, 1:5.5 to 1:12 when n is 2 and 1:6.5 to 1:14 when n is 3.

19. A process according to claim 6, wherein $R_2$ of the carboxylic acid represented by formula (2) is a halogen atom and the reaction is conducted in an inert solvent in the presence of a dehydrohalogenating agent.

20. A process according to claim 19, wherein the dehydrohalogenating agent is a tertiary amine, a pyridine or a metal carbonate.

21. A process according to claim 19, wherein the dehydrohalogenating agent is a piperidinol represented by the formula (3).

22. A process according to claim 19, wherein the dehydrohalogenating agent is used in an amount of 0.8 to 1.2 moles per 1 mole of the piperidinol represented by formula (3).

23. A process according to claim 19, wherein the reaction is conducted at a temperature of −30° to 120° C.

24. A process according to claim 19, wherein the solvent is used in an amount of 0.1 to 30 times the weight of the carboxylic acid represented by formula (2).

25. A process according to claim 19, wherein the mole ratio of the carboxylic acid represented by formula (2) and the piperidinol represented by formula (3) is 1:4.5 to 1:6.0 when n is 1, 1:5.4 to 1:7.2 when n is 2 and 1:6.3 to 1:8.4 when n is 3.

26. A stabilizer for organic substances which contains, as an active component, a piperidine represented by formula (1)

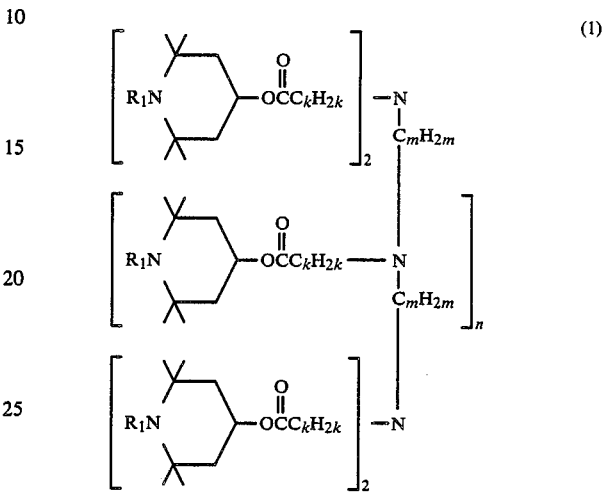

(wherein $R_1$ is a hydrogen atom, an alkyl group of 1 to 3 carbon atoms or a $C_1$–$C_{17}$ alkylcarbonyl group and k, m and n each are an integer of 1 to 3).

27. A stabilizer for organic substances according to claim 26, wherein the organic substance is a synthetic resin or a paint.

28. A stabilizer for organic substances according to claim 27, wherein the active component is contained in an amount of 0.01 to 5 parts by weight per 100 parts by weight of the organic substance.

29. A stabilizer for organic substances according to claim 27, wherein the synthetic resin is a low density polyethylene, a high density polyethylene, a linear low density polyethylene, a chlorinated polyethylene, a polypropylene, a polyvinylchloride, an EVA resin, a PMMA resin, a polystyrene, a high impact polystyrene, an ABS resin, an AES resin, a MBS resin, a polyethylene terephthalate, a polybutylene terephthalate, a polyamide, a polyimide, a polycarbonate, a polyacetal, a polyurethane, an unsaturated polyester resin, or a blend between one of the above mentioned resins and an isoprene rubber, a butadiene rubber, an acrylonitrile-butadiene copolymer rubber, a styrenebutadiene copolymer rubber or an ethylene-propylene copolymer rubber.

30. A stabilizer for organic substances according to claim 27, wherein the paint is an oil paint, an alcohol paint, a cellulose derivative paint, a synthetic resin paint, a synthetic resin emulsion paint or an aqueous baking paint.

31. A stabilizer for organic substances according to claim 26, wherein a phenolic antioxidant is used in combination.

32. A stabilizer for organic substances according to claim 26, wherein a phosphite type antioxidant is used in combination.

33. A stabilizer for organic substances according to claim 26, wherein a sulfur type antioxidant is used in combination.

34. A stabilizer for organic substances according to claim 31, wherein a sulfur type antioxidant is used in combination.

35. A stabilizer for organic substances according to claim 31, wherein a phosphite type antioxidant is used in combination.

36. A stabilizer for organic substances according to claim 34, wherein a phosphite type antioxidant is used in combination.

* * * * *